US009492351B2

(12) United States Patent
Stepovich et al.
(10) Patent No.: US 9,492,351 B2
(45) Date of Patent: Nov. 15, 2016

(54) APPARATUS AND METHODS FOR SEQUESTERING FLUIDS EXHAUSTED DURING FLUID TRANSFER

(75) Inventors: Matthew J. Stepovich, Santa Cruz, CA (US); Randy Kesten, Los Altos, CA (US); Jeff Zalewski, San Francisco, CA (US)

(73) Assignee: ONPHARMA, INC., Los Gatos, CA (US)

(*) Notice: Subject to any disclaimer, the term of this patent is extended or adjusted under 35 U.S.C. 154(b) by 759 days.

(21) Appl. No.: 13/295,408

(22) Filed: Nov. 14, 2011

(65) Prior Publication Data

US 2012/0291909 A1 Nov. 22, 2012

Related U.S. Application Data

(60) Provisional application No. 61/458,002, filed on Nov. 15, 2010.

(51) Int. Cl.
*A61B 19/00* (2006.01)
*A61J 1/20* (2006.01)
*A61J 1/06* (2006.01)

(52) U.S. Cl.
CPC ............. *A61J 1/2075* (2015.05); *A61J 1/2089* (2013.01); *A61J 1/062* (2013.01); *A61J 1/2017* (2015.05)

(58) Field of Classification Search
CPC ...... A61J 1/2075; A61J 1/2089; A61J 1/062; A61J 1/2017
USPC .................................. 604/405, 406, 411–415
See application file for complete search history.

(56) References Cited

U.S. PATENT DOCUMENTS

| | | | |
|---|---|---|---|
| 1,757,809 | A | 5/1930 | Montuori |
| 2,484,657 | A | 10/1949 | Son |
| 2,604,095 | A | 7/1952 | Brody |
| 3,993,791 | A | 11/1976 | Breed et al. |
| 4,154,820 | A | 5/1979 | Simoons |
| 4,259,956 | A | 4/1981 | Ogle |
| 4,630,727 | A | 12/1986 | Feriani et al. |
| 4,654,204 | A | 3/1987 | Copenhafer et al. |
| 4,756,838 | A | 7/1988 | Veltman et al. |
| 4,959,175 | A | 9/1990 | Yatzidis |
| 5,062,832 | A | 11/1991 | Seghi |
| 5,137,528 | A | 8/1992 | Crose |
| 5,149,320 | A | 9/1992 | Dhaliwal et al. |

(Continued)

FOREIGN PATENT DOCUMENTS

| | | |
|---|---|---|
| CN | 1154657 A | 7/1997 |
| EP | 1858578 A2 | 11/2007 |

OTHER PUBLICATIONS

International search report and written opinion dated Mar. 9, 2012 for PCT/US2011/060653.

(Continued)

*Primary Examiner* — Leslie Deak
(74) *Attorney, Agent, or Firm* — Thompson Hine LLP

(57) ABSTRACT

A liquid transfer connector comprises an enclosure holding a transfer needle and an exhaust needle. A container of donor liquid may be attached to an inlet end of the transfer needle and a container holding a recipient liquid may be attached to an outlet end of the transfer needle and an inlet end of an exhaust needle. The exhaust needle has an outlet end within the connector which releases displaced fluid into an absorbent mass which sequesters the fluid to prevent leakage.

22 Claims, 3 Drawing Sheets

(56) References Cited

U.S. PATENT DOCUMENTS

| | | | |
|---|---|---|---|
| 5,188,614 A | | 2/1993 | Hart |
| 5,226,901 A | | 7/1993 | Dhaliwal et al. |
| 5,296,242 A | | 3/1994 | Zander |
| 5,330,426 A | | 7/1994 | Kriesel et al. |
| 5,383,324 A | | 1/1995 | Segers et al. |
| 5,603,695 A | | 2/1997 | Erickson |
| 5,609,838 A | | 3/1997 | Neuman et al. |
| 5,674,195 A | | 10/1997 | Truthan |
| 5,779,357 A | | 7/1998 | Jonsson et al. |
| 5,984,906 A | | 11/1999 | Bonnichsen et al. |
| 5,985,434 A | * | 11/1999 | Qin et al. .................. 428/315.5 |
| 6,022,337 A | | 2/2000 | Herbst et al. |
| 2004/0175437 A1 | | 9/2004 | Beckett |
| 2007/0060904 A1 | | 3/2007 | Vedrine et al. |
| 2007/0208296 A1 | | 9/2007 | Paproski et al. |
| 2009/0292271 A1 | | 11/2009 | Stepovich et al. |
| 2011/0166543 A1 | | 7/2011 | Stepovich et al. |

OTHER PUBLICATIONS

European Patent Office, Supplementary European Search Report issued in corresponding Application No. 11842038.9 dated Sep. 14, 2015, 7 pages.

IP Australia, Patent Examination Report No. 1, issued in corresponding Application No. 2011329122 dated Apr. 2, 2015, 3 pages.

China Patent&Trademark Office, Official Action and translation issued in application No. 201180063000.0 dated Oct. 23, 2014.

* cited by examiner

APPARATUS AND METHODS FOR SEQUESTERING FLUIDS EXHAUSTED DURING FLUID TRANSFER

CROSS-REFERENCES TO RELATED APPLICATIONS

The present application claims the benefit of provisional No. 61/458,002, filed on Nov. 15, 2010, the full disclosure of which is incorporated herein by reference.

BACKGROUND OF THE INVENTION

1. Field of the Invention

The present invention relates generally to methods and apparatus for combining parenteral solutions and other liquids. More particularly, the present invention relates to methods for transferring a donor liquid into a recipient container filled with a recipient liquid where excess liquid in the recipient container is exhausted from the recipient container and captured.

Commonly-owned copending application US 2009/0292271, the full disclosure of which is incorporated herein by reference, describes a "dosing pen" device capable of combining liquid buffers and anesthetics. The dosing pen includes a fluid transfer device which utilizes a transfer needle 36 (the reference numbers in this paragraph refer to the '271 publication) and an exhaust needle 38 positioned in a knob 12 which can removably receive an anesthetic cartridge 28 so that distal ends of both the transfer needle and exhaust needle penetrate a septum on the anesthetic cartridge. A buffer cartridge 16 positioned within a housing 14 is also attached to the knob 12 so that a proximal end 50 of the transfer needle 36 can penetrate a septum 15 of the buffer cartridge when the knob is fully advanced onto the housing. A pusher 20 is provided to drive a plunger 58 on the buffer cartridge to transfer buffer through transfer needle 36 into the anesthetic cartridge 28 and to simultaneously exhaust anesthetic from the anesthetic cartridge back into a reservoir 72 in the housing 14 through the exhaust needle 38. While the dosing pen of the '271 application is advantageous in many respects, the excess buffer, which is exhausted through exhaust needle 38, ends up in the housing 14 and is subject to leakage.

An improved dosing pen is described in commonly owned US2011/0166543, the full disclosure of which is incorporated herein by reference. As illustrated in FIG. 1 herein, the '543 publication shows a dosing assembly 10 which connects a buffer cartridge 12 and an anesthetic cartridge 14 with a transfer needle 16 entering through septum 18 and septum 20, respectively. An exhaust needle penetrates septum 20 of the anesthetic cartridge and allows excess anesthetic to vent into a collection reservoir 26 in a housing 24 which hold the needles. The chamber is "sealed" and intended to be contain the excess liquid 28 to prevent leakage. While certainly an improvement, the chamber will usually need at least a small vent to permit the displacement of air initially present in the chamber and remains subject to leakage as the dosing pen is manipulated and reoriented, particularly when a new anesthetic cartridge is being exchanged for a buffered anesthetic cartridge. Even if leakage through the vent were inhibited, for example using a gas permeable liquid barrier over the vent, there is still a risk that pooled liquid within the chamber could submerge the outlet end of the exhaust needle, resulting in backflow of the excess fluid.

For these reasons, it would be desirable to provide improved methods and apparatus for transferring and combining liquids, such as buffer solutions and anesthetics, where the liquids are held in conventional containers with needle-penetrable septums and dispensing plungers. In particular, it would be desirable to provide systems and methods which allow for transfer of a donor liquid, such as a buffer solution, into a recipient solution, such as an anesthetic, which fills a recipient container where the displaced recipient solution can be vented or exhausted into a reservoir with a minimum risk of backflow or leakage from the reservoir. At least some of these objectives will be met by the inventions described hereinbelow.

2. Description of the Background Art

US 2011/0166543 and US2009/0292271 have been described above. Glass vials and cartridges for storing medical solutions are described in U.S. Pat. Nos. 1,757,809; 2,484,657; 4,259,956; 5,062,832; 5,137,528; 5,149,320; 5,226,901; 5,330,426; and 6,022,337. Injection pens which employ drug cartridges are described in U.S. Pat. No. 5,984,906. A particular disposable drug cartridge that can find use in the present invention is described in U.S. Pat. No. 5,603,695. A device for delivering a buffering agent into an anesthetic cartridge using a transfer needle is described in U.S. Pat. No. 5,603,695. Other patents and applications of interest include U.S. Pat. Nos. 2,604,095; 3,993,791; 4,154,820; 4,630,727; 4,654,204; 4,756,838; 4,959,175; 5,296,242; 5,383,324; 5,603,695; 5,609,838; 5,779,357; and U.S. Patent Publ. No. 2004/0175437

BRIEF SUMMARY OF THE INVENTION

The present invention provides apparatus and methods which rapidly absorb liquids displaced during fluid transfer into a sealed recipient container. While particularly useful when transferring a buffer solution into an anesthetic or other medical solution, the apparatus and methods of the present invention will also be useful whenever a donor fluid is being transferred into a recipient fluid held in a closed container where a volume of the recipient fluid equal to the volume of the donor fluid being transferred must be vented or exhausted from the closed container. In particular, the present invention provides structures and materials which capture and rapidly absorb the exhausted recipient fluid so that the risk of leakage of the recipient fluid is reduced or eliminated.

Apparatus according to the present invention comprise a liquid transfer connector for providing a liquid transfer path between a donor container having a needle-penetrable septum and a recipient container having a needle-penetrable septum. The connector comprises an enclosure having an interior chamber with a vent, typically a small orifice or a hole in a wall of the chamber which allows air in the chamber to be released while a displaced fluid is collected in the interior chamber. A transfer needle has an inlet end extending from one side of the interior chamber and an outlet end extending from another side of the chamber, where both the inlet end and the outlet end are capable of penetrating a septum on a liquid container. Usually, the transfer needle will be straight so that the inlet and outlet ends are disposed on opposite sides of the chamber, but in other instances the needle could be non-linear and even U-shaped so that the "sides" of the chamber could be adjacent to each other. The connector further includes an exhaust needle having an inlet end adjacent to the outlet end of the transfer needle and an outlet end in the interior chamber. The inlet end of the exhaust needle will also be capable of penetrating a septum on a liquid container, but the outlet end need not be. A liquid-absorptive mass is located within the interior chamber and adapted for rapid absorption of liquid entering the interior chamber through the exhaust needle. In this way, the liquid is captured and sequestered within the absorptive mass so that little or no free liquid remains in the chamber, thus reducing or eliminating the risk that the liquid will be lost through the vent, via backflow through the exhaust needle, or in any other way.

In specific aspects of the present invention, the absorptive mass has a structure and is formed from materials which optimize the rapid absorption of the liquid as it enters the interior chamber. The absorbent mass is preferably formed from a liquid-absorptive open-cell foam having a high porosity, typically above 75% porosity, preferable above 80% porosity, and typically 90% porosity or above, where porosity is defined as the percentage of void volume within the total volume of the absorptive mass. In addition to the high porosity, it is desirable that the liquid-absorptive foam have a rapid liquid absorption rate, preferably having a liquid absorbency time of 10 seconds, or below, preferably 5 seconds or below. The liquid absorbency time may be measured using the methods described in IS09073-6-2000, “Textiles-Test methods for non-wovens-Part 6: Absorption,” section 4, available from the International Organization of Standards, Geneva, Switzerland (www.iso.org). The test measures how rapidly a standard volume and weight of an absorptive materials can absorb liquid, where a shorter time indicates a more rapidly absorptive material. A particularly preferred liquid-absorptive foam materials is a foam formed from polyvinyl acetal (PVA) resin, which is a thermoplastic resin formed by the condensation of an aldehyde with a polyvinyl alcohol. A particularly useful TVA foam is available from PVA Unlimited (Wausau, Indiana).

In addition to the material, the structure or geometry of the liquid-absorptive mass can also be selected to promote rapid absorption and sequestration of the exhausted recipient liquid entering the interior chamber of the connector. While the geometry can be as simple as terminating an end of the exhaust needle near the center of the absorptive mass and/or providing a plurality of outlet ports or branches on the exhaust needle, it will be preferred to provide an interior void within the absorptive mass where the outlet end of the exhaust needle is spaced-apart from the walls of the interior void so that the exhausted recipient liquid can pool in the void without submerging the outlet end of the exhaust needle. Such interior void provides both a retention volume for holding the surge of liquid which result from a liquid introduction into the closed recipient container and a large but contained surface area over which the exhausted recipient liquid can penetrate into the internal pores of the absorptive mass while containing the liquid within the void of the absorptive mass even prior to absorption.

In another specific aspect, the enclosure of the liquid transfer connector may comprise a cylindrical sleeve having a partition which separates an attachment receptacle that encloses the outlet end of the transfer needle and the inlet end of the exhaust needle from the interior chamber. The transfer needle may pass axially through the liquid absorptive mass, but in other embodiments could pass outside of the mass in either a linear or non-linear configuration. The liquid transfer connectors may also be incorporated into the dosing pins described in commonly owned publications US2009/0292271 and US2011/0166543, the full disclosures of which have previously been incorporated herein by reference.

Methods according to the present invention transfer a donor liquid into a recipient liquid present in a closed container. The methods comprise establishing a transfer flow path from a source of the donor liquid into the closed container which is filled with the recipient liquid, typically with little or no head space so that transfer of the donor liquid requires displacement of the recipient liquid from the closed container. To displace the recipient liquid, an exhaust flow path is established from the closed container to an absorbent mass capable of absorbing and sequestering the recipient liquid. Thus, by causing a volume of the donor liquid to flow into the closed container through the transfer flow path, a like volume of the recipient liquid is caused to flow through the exhaust flow path into the absorbent mass, where the entire volume of the exhausted recipient liquid is absorbed by the absorbent mass.

In a specific aspect of the present invention, the outlet end of transfer needle extends further into the recipient container than does the inlet end of the exhaust needle. Such an axial offset reduces the risk that the donor liquid will “short circuit” and be exhausted from the recipient container. Ideally, only recipient liquid will be exhausted but it is possible of course that a small amount of the donor liquid will be mixed with the exhausted recipient liquid.

As described above with respect to the apparatus of the present invention, the absorbent mass is usually at least partially formed from a liquid-absorptive foam where the foam has an absorptive rate less than 10 seconds. Preferred liquid-absorptive foam materials comprise a polyvinyl acetal resin, and the absorptive mass preferably comprises a block of the absorptive material having an interior void which surrounds the outlet end of the exhaust needle.

In other specific aspects of the methods of the present invention, the absorptive mass will have an absorptive capacity equal to at least twice that of the volume of the exhausted recipient liquid, preferably being at least four times as great, and often being ten times as great or more. In this way, the absorptive mass can be used for multiple fluid transfers, optionally where the recipient liquid container and/or a donor liquid container is replaced while using the same liquid transfer connector. Additionally, the interior void will typically have a volume equal to at least the volume of the exhausted recipient liquid, but preferably will have a volume equal to two, four, or more times the expected volume of the exhausted recipient liquid. Further, the end of the exhaust needle will usually be spaced apart from the walls of the interior void so that the exhausted recipient liquid can pool in the void without submerging the outlet end, thus reducing or eliminating the risk of backflow of the liquid into the outlet end of the exhaust needle.

BRIEF DESCRIPTION OF THE DRAWINGS

In order to better understand the invention and to see how it may be carried out in practice, some preferred embodiments are next described, by way of non-limiting examples only, with reference to the accompanying drawings, in which like reference characters denote corresponding features consistently throughout similar embodiments in the attached drawings.

DETAILED DESCRIPTION OF THE INVENTION

Figure 1:
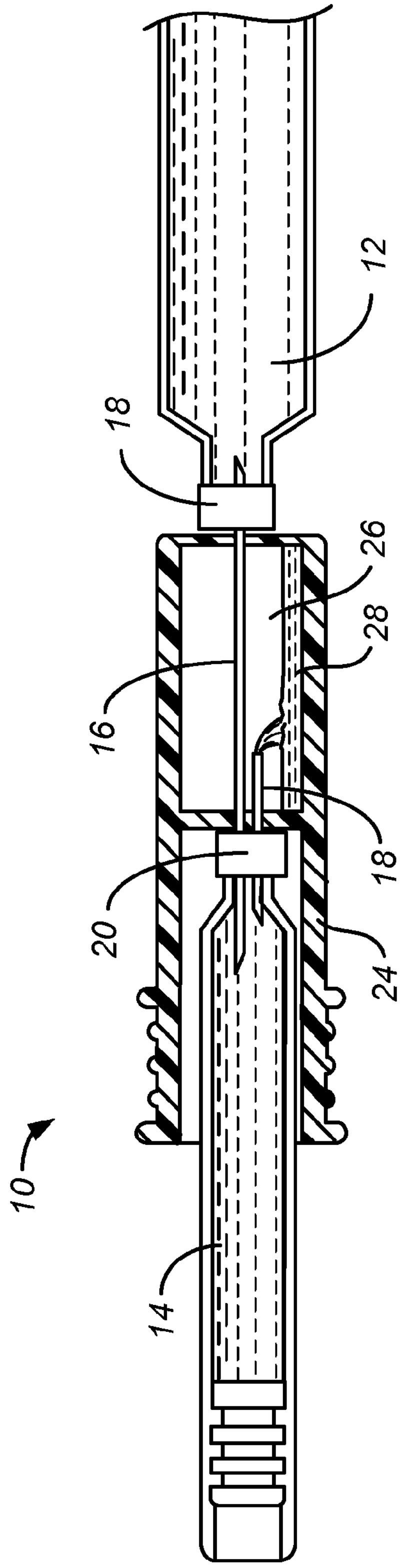
FIG. 1 (PRIOR ART)
FIG. 1 illustrates a prior art liquid transfer connector having a sealed liquid collection reservoir.
Figure 2A:
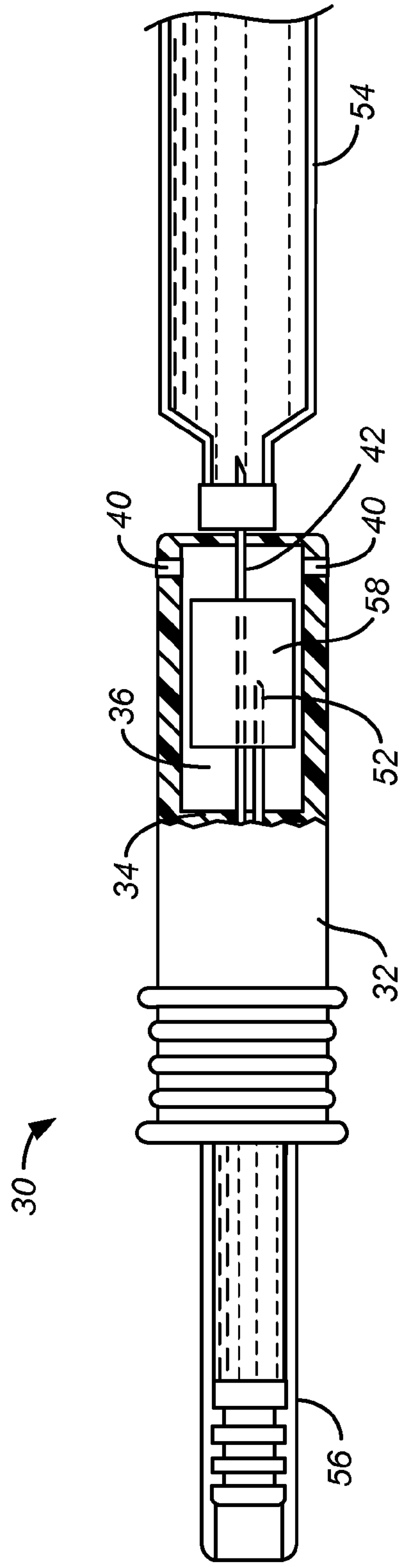
FIGS. 2A and 2B illustrate a liquid transfer connector constructed in accordance with the principles of the present invention and having a liquid absorptive mass for sequestering displaced recipient liquid.
Figure 2B:
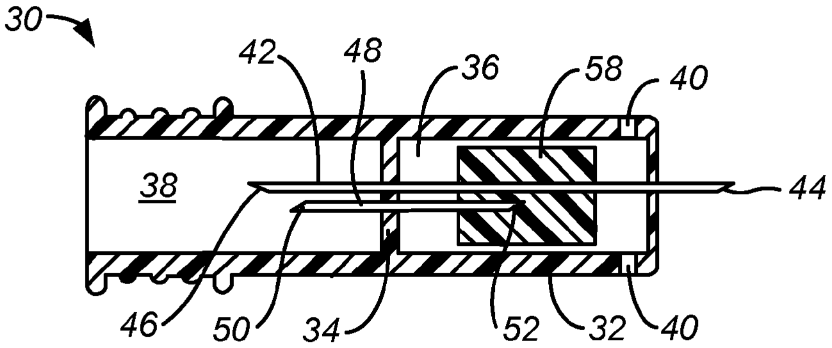

Referring to FIGS. 2A and 2B, a liquid transfer connector 30 constructed in accordance with the principles of the present invention comprises an enclosure 32 having an open interior with a partition 34 separating an interior chamber 36 from an attachment receptacle 38 (FIG. 2B). The interior chamber 36 is generally closed but includes vents 40 which allow displaced gas to exit the chamber when displaced liquid enters the chamber, as described in more detail below. The vents 40 may be simple openings in a wall of the enclosure which are sized and shaped to permit the passage of gas while optionally (although not necessarily) inhibiting liquid flow. Further optionally, the vents 40 may have a gas permeable but liquid impenetrable matrix or other material therein or thereover to allow gases to vent but retain liquids.

A liquid transfer needle 42 is attached to the enclosure, typically being fixed through the partition 34, such that an inlet and 44 is disposed on one side of the interior chamber 36 and an outlet end 46 is disposed on another side of the chamber, typically within the attachment receptacle 38. An exhaust needle 48 is also secured to the enclosure 32 and will have an inlet end 50 dispose near but axially offset from the outlet end 46 of the transfer needle since both the outlet end 46 and the inlet end 50 must penetrate through the septum of a single recipient container 56 as part of the fluid transfer procedure. An outlet end 52 of the exhaust needle 48 will be positioned within the interior chamber 36 and disposed to a release exhausted recipient liquid into an absorbent mass 58 also located within the interior chamber 36. Inlet end 44 of the transfer needle 42 will be available to penetrate the septum of a container 54 of the donor liquid which is to be transferred into the recipient liquid in container 56.

Transfer of the donor liquid from container 54 into the recipient liquid in container 56 is typically achieved by displacing a plunger (not shown) on the donor container so that liquid flows through the transfer needle 42 into the interior of the recipient container 56. As the recipient container 56 will typically be completely filled with the recipient liquid, entry of the donor liquid will cause a like volume of the recipient liquid to be exhausted through the exhaust needle 48 and into the absorptive mass 58 where it is sequestered and prevented from leaking through the vents 40, backflows into the exhaust needle 48, or otherwise being lost. Of course, it will be understood that a small portion of the donor liquid may be mixed in with the recipient liquid which is exhausted, but the amount of donor liquid in the exhausted liquid will usually be minimized, typically by offsetting the inlet end 50 of the exhaust needle 48 from the outlet end 46 of the transfer needle 42.

Figure 3A:
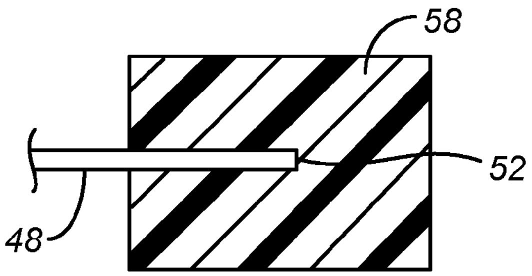
FIGS. 3A-3C illustrate alternative embodiments of the liquid absorptive mass of the present invention.
Figure 3B:
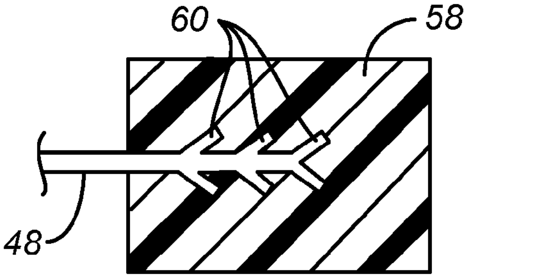
Figure 3C:
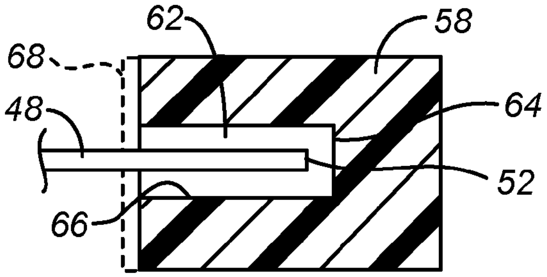

Referring now to FIGS. 3A-3C, the absorbent mass may have a variety of geometries intended to promote capture and sequestration the exhaust recipient liquid so that the liquid is not allowed to backflow into the outlet end 52 of exhaust needle 48 or leak into the interior chamber 36 from where it might leak outside of the liquid transfer connector 30. As shown in FIG. 3A, the absorbent mass could be a block with the outlet in 52 of the exhaust needle 48 terminating generally at a mid or center point within the mass. While having the advantage of being a simple design, the limited area of the mass exposed to the needle limits release of the liquid and can cause back pressure and potential back flow of the liquid along the needle so that it is lost in the absorptive mass if the liquid transfer rate is too great.

Alternatively, the absorptive mass 58 may comprise absorbent beads having a size or shape which prevents passage through the vents. The interior chamber 36 may be loose packed with such beads and the very large surface area will result in rapid absorption of liquid released by the exhaust needle 48. Typically the absorptive mass will be formed from a material that does not biologically and/or chemically react with the recipient liquid.

An alternative absorptive mass configuration is illustrated in FIG. 3B where the exhaust needle 48 comprised a plurality of branches or ports 60 along its length which distribute the exhausted recipient liquid to a plurality of locations within the absorptive mass, thus reducing the back pressure and allowing greater fluid transfer rates without leakage. Although an improvement, this design is more difficult to construct and implement.

A presently preferred design for the absorptive mass 58 is illustrated in FIG. 3C. There, the absorptive mass comprises an outer block or shell surrounding an interior void 62, where the outlet end 52 of the exhaust needle 48 is located near an interior end 64 of the void but spaced well apart from the side walls 66 of the void. This construction allows the liquid to enter freely (with minimum back pressure) into the void 62 where it can be temporarily collected, distributed around the walls of the void, and absorbed into the absorptive mass 58 before having an opportunity to backflow into outlet end 52 of exhaust needle 48 or otherwise leak from the void. Optionally, a gas permeable liquid barrier 68 may be formed over the open end of the void to further inhibit loss of free liquid from the void.

Figure 4A:
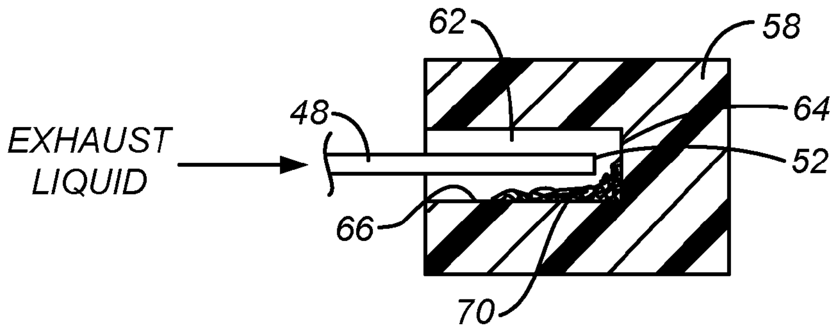
FIGS. 4A-4D illustrate how a displaced recipient liquid is absorbed within a liquid absorptive mass during a liquid transfer protocol in accordance with the principles of the present invention.
Figure 4B:
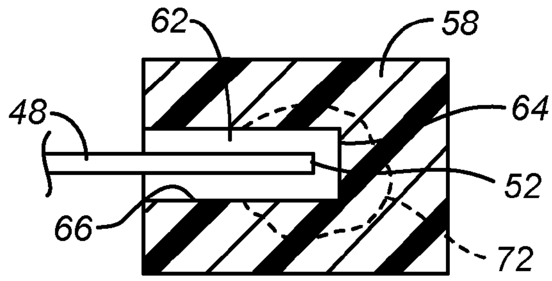
Figure 4C:
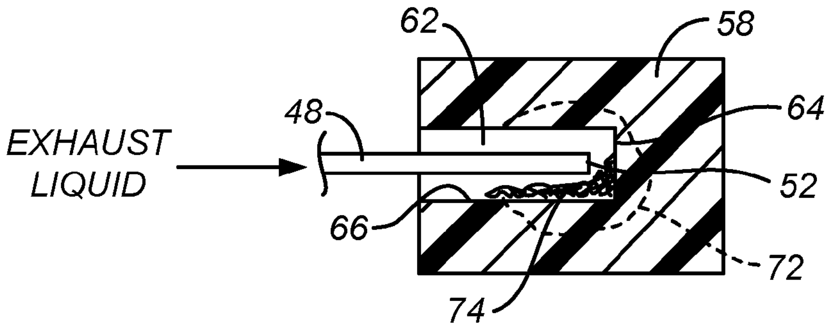
Figure 4D:
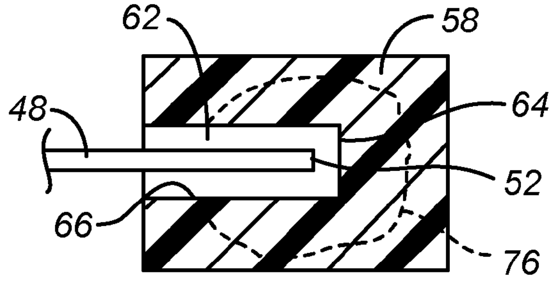

As shown in FIGS. 4A-4D, sequential absorption of volumes of displaced recipient fluid exhausted through needle 48 into the absorptive mass 58 of FIG. 3C is illustrated. Usually, a first volume of the exhausted liquid is released into the interior void 62 from the outlet end 52 of the exhaust needle 48. The liquid will initially remain within the void and distribute over portions of the end wall 64 and side wall 66. The distributed liquid will immediately begin to be absorbed into the mass where it becomes sequestered and inhibited from release. The volume of the interior void 62 will be greater than that of the expected volume of exhaust liquid expected to be released at any one time, typically being at least twice the expected volume, and often being many times greater. After the first volume of exhausted liquid is absorbed into the absorptive mass 48, the liquid will penetrate into the mass along a boundary line 72, as shown in FIG. 4B. Typically, the entire volume of the absorptive mass 58 will be many times greater than the expected volume of each release of exhaust liquid. Thus, multiple fluid transfers and exhaust liquid releases may be performed before it is time to either dispose of the liquid transfer connector or replace the absorptive mass within the interior chamber 36. The release of a second volume of the exhaust liquid is illustrated in FIG. 4C. The liquid 74 will typically distribute along the back wall 64 and side walls 66 generally in the same manner as in the first release. After the second volume is released, the peripheral absorption within the mass 58 will be greater, as illustrated at boundary line 76 in FIG. 4D.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A liquid transfer connector for providing a liquid transfer path between a donor container having a needle-penetrable septum and a recipient container having a needle-penetrable septum, said connector comprising:

an enclosure having an interior chamber with a vent;

a transfer needle having an inlet end extending from one side of the interior chamber and an outlet end extending from another side of the interior chamber, wherein both the inlet end and the outlet end are capable of penetrating a septum on a liquid container;

an exhaust needle having an inlet end adjacent to the outlet end of the transfer needle and an outlet end in the interior chamber; and a liquid-absorptive mass within the interior chamber, said liquid-absorptive mass adapted for rapid absorption of liquid entering the interior chamber through the exhaust needle.

2. A connector as in claim 1, wherein the liquid-absorptive mass is at least partially formed from a liquid-absorptive foam.

3. A connector as in claim 2, wherein the liquid-absorptive foam has an absorptive rate less than 10 seconds as measured by IS09073-6-2000.

4. A connector as in claim 3, wherein the liquid-absorptive foam comprises a polyvinyl acetal resin.

5. A connector as in claim 1, wherein the liquid-absorptive mass comprises a block of absorptive material having an interior void which surrounds the outlet end of the exhaust needle.

6. A connector as in claim 5, wherein the outlet end of the exhaust needle is spaced apart from walls of the interior void so that the exhausted recipient liquid can pool in the void without submerging the inlet end.

7. A connector as in claim 1, wherein the liquid-absorptive mass comprises absorbent beads having a size or shape which prevents passage through the vents.

8. A connector as in claim 7, wherein the absorbent beads are loose and fill the interior chamber.

9. A connector as in claim 1, wherein the enclosure comprises a cylindrical sleeve having a partition which separates an attachment receptacle that encloses the outlet end of the transfer needle and the inlet end of the exhaust needle from the interior chamber.

10. A connector as in claim 1, wherein the transfer needle passes axially through the liquid-absorptive mass.

11. A method for transferring a donor liquid into a recipient liquid present in a closed container, said method comprising:

establishing a transfer flow path from a source of the donor liquid into the closed container filled with the recipient liquid;

establishing an exhaust flow path from the closed container to an absorbent mass; and causing a volume of the donor liquid to flow into the closed container through the transfer flow path which in turn causes a like volume of the recipient liquid to flow through the exhaust flow path into the absorbent mass, wherein the entire volume of the exhausted recipient liquid is absorbed by the absorbent mass.

12. A method as in claim 11, wherein the absorbent mass is at least partially formed from a liquid-absorptive foam.

13. A method as in claim 12, wherein the liquid-absorptive foam has an absorptive rate less than 10 seconds as measured by IS09073-6-2000.

14. A method as in claim 13, wherein the liquid-absorptive foam comprises a polyvinyl acetal resin.

15. A method as in claim 11, wherein the absorbent mass comprises absorbent beads having a size or shape which prevents passage through the vents.

16. A method as in claim 15, wherein the absorbent beads are loose and fill the interior chamber.

17. A method as in claim 11, wherein the absorbent mass comprises a block of absorptive material having an interior void which surrounds an outlet end of the exhaust needle.

18. A method as in claim 11, wherein the absorbent mass has an absorptive capacity equal to at least twice the volume of the donor liquid.

19. A method as in claim 17, wherein the interior void has a volume equal to at least the volume of the donor liquid.

20. A method as in claim 17, wherein the outlet end of the exhaust needle is spaced apart from walls of the interior void so that the exhausted recipient liquid can pool in the interior void without submerging the outlet end.

21. A method as in claim 11, wherein the absorbent mass comprises a material that does not biologically or chemically react with the recipient liquid.

22. A connector as in claim 1, wherein the liquid-absorptive mass comprises a material that does not biologically or chemically react with the recipient liquid.

* * * * *